United States Patent [19]

Adams, Jr.

[11] 4,311,696

[45] Jan. 19, 1982

[54] SUBSTITUTED BUTANOIC ACID ESTERS

[75] Inventor: John B. Adams, Jr., Hockessin, Del.

[73] Assignee: E. I. Du Pont de Nemours and Company, Wilmington, Del.

[21] Appl. No.: 233,770

[22] Filed: Feb. 12, 1981

[51] Int. Cl.³ .................. C07C 117/04; A61K 31/655
[52] U.S. Cl. ..................................... 424/226; 260/349
[58] Field of Search ......................... 260/349; 424/226

[56] References Cited

U.S. PATENT DOCUMENTS 3,996,244 12/1976 Fujimoto et al. ................ 260/340.5
4,058,622 11/1977 Fujimoto et al. ..................... 560/81

*Primary Examiner*—John M. Ford
*Assistant Examiner*—Jane T. Fan

[57] ABSTRACT

The substituted butanoic acid esters 2-(4-azidophenyl)-3-methylbutanoic acid, α-cyano-3-phenoxybenzyl ester and 2-(4-azidophenyl)-3-methylbutanoic acid, 3-phenoxybenzyl ester are useful as insecticides.

4 Claims, 9 Drawing Figures

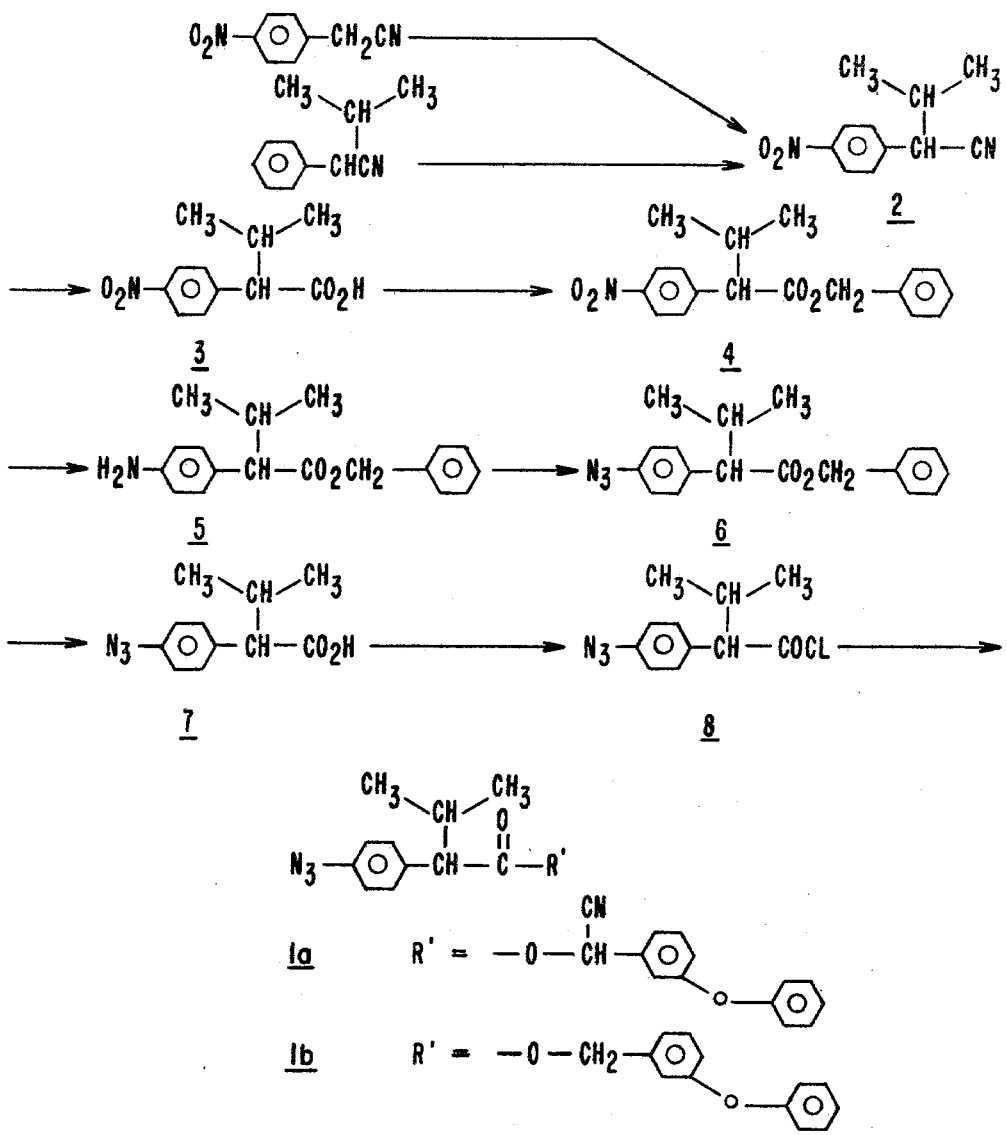

SUBSTITUTED BUTANOIC ACID ESTERS

BACKGROUND OF THE INVENTION

This invention relates to insecticidal butanoic acid esters.

Belgian Pat. No. 801,946 discloses benzeneacetic acid esters as insecticides, and includes a commercially available compound,

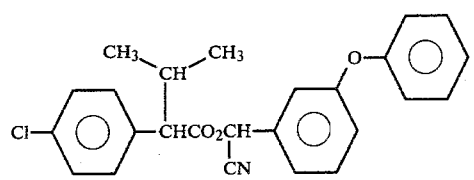

A substantial portion of the world's food supply is destroyed by pests and plant diseases. There is thus a continuing need for highly active insecticides.

SUMMARY OF THE INVENTION

Two new compounds have now been found which have insecticidal activity: 2-(4-azidophenyl)-3-methylbutanoic acid, α-cyano-3-phenoxybenzyl ester and 2-(4-azidophenyl)-3-methylbutanoic acid, 3-phenoxybenzyl ester. These compounds can be represented by Formula I:

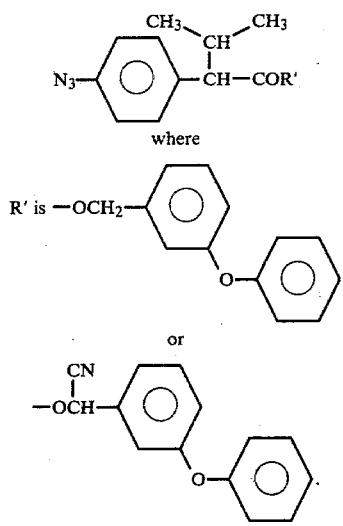

This invention thus relates to the compounds of Formula I, to insecticidal compositions containing them and to the method of using them as insecticides.

This invention also relates to the novel compounds of Formula II which are useful as intermediates in preparing compounds of Formula I.

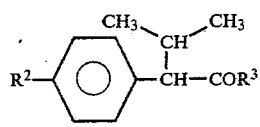

where
$R^2$ is $NH_2$ or $N_3$; and $R^3$ is benzyloxy, m-phenoxybenzyloxy, $C_1$–$C_4$ alkoxy, OH or Cl; provided that, when $R^2$ is $NH_2$, then $R^3$ is other than OH or Cl.

Compounds within the scope of Formula II include, among others:
2-(4-aminophenyl)-3-methylbutanoic acid, benzyl ester;
2-(4-azidophenyl)-3-methylbutanoic acid, benzyl ester;
2-(4-azidophenyl)-3-methylbutanoic acid;
2-(4-azidophenyl)-3-methylbutanoyl chloride;
2-(4-aminophenyl)-3-methylbutanoic acid, methyl ester;
2-(4-azidophenyl)-3-methylbutanoic acid, methyl ester;
2-(4-aminophenyl)-3-methylbutanoic acid, butyl ester;
2-(4-azidophenyl)-3-methylbutanoic acid, butyl ester;
2-(4-aminophenyl)-3-methylbutanoic acid, m-phenoxybenzyl ester; and
2-(4-azidophenyl)-3-methylbutanoic acid, m-phenoxybenzyl ester.

DETAILED DESCRIPTION OF THE INVENTION

Preparation

The schematic diagram shown in the attached drawing describes preparation of the esters of this invention, represented by 1a and 1b. Although the literature implies that intermediate compounds 2 and 3 are known, directions for their preparation and description of their properties are scant and are therefore described here.

4-Nitrobenzyl cyanide is treated with potassium methoxide in dimethyl sulfoxide (DMSO), followed by 2-iodopropane, effecting alkylation and providing 2 as a distillable and recrystallizable compound. Alternatively, 2-phenyl-3-methylbutyronitrile can be nitrated directly at low temperatures to provide compound 2.

Acid-catalyzed hydrolysis of 2 by methods well known in the art (e.g., boiling 70% $H_2SO_4$) provides the carboxylic acid 3.

Acid-catalyzed esterification of 3 with the appropriate alcohol (benzyl alcohol shown) provides the ester 4 (benzyl ester shown).

Chemical reduction of the nitro group in 4, e.g., with iron in aqueous acetic acid, provides the amino compound 5.

Diazotization of the amino compound 5 and addition of the diazonium compound to aqueous sodium azide provides the azido compound 6.

Saponification of the ester group in 6, and subsequent acidification, provides the carboxylic acid 7.

Conversion of the carboxylic acid 7 to the acid chloride 8 can be accomplished with thionyl chloride, optionally in the presence of N,N-dimethylformamide (DMF) as a catalyst.

The acid chloride 8 is then converted to the ester 1a or 1b by reaction with the appropriate alcohol in the presence of an acid acceptor, such as triethylamine.

The preparation of the compounds of this invention is further illustrated by the following examples. In these examples, all percentages are by weight and temperatures in degrees centigrade unless otherwise indicated.

EXAMPLE 1a 2-(4-Nitrophenyl)-3-methylbutyronitrile—by alkylation

To a nitrogen-blanketed solution of 110.8 g of 4-nitrobenzyl cyanide in 500 ml of DMSO was added 50.3 g of potassium methoxide in several portions while the temperature was held at ≦27°. To the purple solution was added 75.1 ml of 2-iodopropane. A slow, persistent exotherm ensued, and the temperature was maintained at ambient. After 17 hours, the reaction mixture was poured into excess ice-water and mixed with butyl chloride. Following filtration on glass wool, the layers were separated and the butyl chloride solution washed with water and saturated sodium bicarbonate solution (3 times), then dried over a mixture of MgSO$_4$, NaHCO$_3$ and silica gel. Filtration and removal of the solvent in vacuum provided 116 g of a dark red-orange oil. Vacuum distillation provided 99.6 g of yellow oil (bp 140°–153°/0.5 Torr), which solidified. Recrystallization from butyl chloride/hexane provided 2-(4-nitrophenyl)-3-methylbutyronitrile of m.p. 71°–72°, with white to pale-yellow color.

Anal. Calcd. for C$_{11}$H$_{12}$N$_2$O$_2$: C, 64.7; H, 5.9; N, 13.7%. Anal. Found: C, 64.8; H, 6.0; N, 13.9%.

EXAMPLE 1b 2-(4Nitrophenyl)-3-methylbutyronitrile—by nitration

Into mixed acids (5 ml of 90% nitric acid and 60 ml of concentrated sulfuric acid), held at −2° to −3° with a dry-ice/acetone bath, was dripped 15.92 g of 2-phenyl-3-methylbutyronitrile, causing a very exothermic reaction during the 7-minutes addition period. After an additional 70 minutes at −5° to 0°, the dark reddish orange reaction mixture was poured into excess ice. The thick oil which formed was extracted into butyl chloride, and the butyl chloride extract washed twice each with water and saturated sodium bicarbonate solution. Drying (MgSO$_4$) and evaporation of the butyl chloride solution provided an orange-yellow oil. Vacuum distillation gave 17.1 g of yellow oil, bp 118°–130°/(0.2–0.3 Torr). Crystallization from butyl chloride/hexane provided white 2-(4-nitrophenyl)-3-methylbutyronitrile of m.p. 69°–71°.

EXAMPLE 2

2-(4-Nitrophenyl)-3-methylbutanoic acid

A mixture of 82.4 g of 2-(4-nitrophenyl)-3-methylbutyronitrile and 603 g of 70% sulfuric acid was boiled under reflux for 1 hour, then cooled to 120° and cautiously diluted with ice and water to a total volume of 1.5 l. The solid was filtered off, washed with water, and extracted with several portions of hot 6% potassium carbonate solution. The carbonate solution was treated with activated carbon, filtered, and slowly acidified with concentrated hydrochloric acid, precipitating white solid. The solid was filtered from the cooled mixture and dried to 81 g of 2-(4-nitrophenyl)-3-methylbutanoic acid, m.p. 124°–127°.

Anal. Calcd. for C$_{11}$H$_{13}$NO$_4$: C, 59.2; H, 5.9; N, 6.3%; Anal. Found: C, 59.2; H, 6.0; N, 6.4%.

EXAMPLE 3

2-(4-Nitrophenyl)-3-methylbutanoic acid, benzyl ester

A mixture of 80.1 g of 2-(4-nitrophenyl)-3-methylbutanoic acid, 150 ml of benzyl alcohol, 75 ml of toluene and 2 g of p-toluenesulfonic acid monohydrate was boiled under reflux, with azeotropic removal of water, for 10 hours. The toluene and excess benzyl alcohol were removed in vacuum, and the residual oil was dissolved in butyl chloride. The butyl chloride solution was washed with 6% potassium carbonate three times (acidification of the carbonate extract precipitated 5.2 g of the starting carboxylic acid), water and saturated brine. The dried (MgSO$_4$) butyl chloride solution was evaporated to a residual oil. The oil was vacuum distilled, the bulk of it boiling at 197°–200°/0.3 Torr, providing 99 g of 2-(4-nitrophenyl)-3-methylbutanoic acid, benzyl ester as a yellow oil.

Anal. Calcd. for C$_{18}$H$_{19}$NO$_4$: C, 69.0; H, 6.1; N, 4.5%. Anal. Found: C, 70.4; H, 6.2; N, 4.2%.

EXAMPLE 4

2-(4-Aminophenyl)-3-methylbutanoic acid, benzyl ester

Iron powder, 55 g, was added in portions to a stirred mixture of 94.6 g of 2-(4-nitrophenyl)-3-methylbutanoic acid, benzyl ester, 400 ml of acetic acid, and 100 ml of water. The temperature was kept at 90°–95° by occasional application of an ice bath. After an additional 20 minutes at 90°–95°, the hot mixture was filtered, and the filtrate was diluted with water, precipitating an oil. The oil was extracted into butyl chloride, and the butyl chloride solution washed with water (3 times) and saturated sodium bicarbonate solution, dried (MgSO$_4$) and evaporated to 85.7 g of orange oil, 2-(4-aminophenyl)-3-methylbutanoic acid, benzyl ester. Mass spectral analysis shows the expected molecular ion, m/e 283, of the product.

EXAMPLE 5

2-(4-Azidophenyl)-3-methylbutanoic acid, benzyl ester

To a stirred solution of 20 ml of water and 11 ml of concentrated hydrochloric acid at <10° was added a solution of 14.17 g of 2-(4-aminophenyl)-3-methylbutanoic acid, benzyl ester in 50 ml of acetic acid. At 0° to 5° was added a solution of 3.62 g of sodium nitrite in 12.5 ml of water. The mixture was stirred at 0° to 5° for an additional 45 minutes, then poured into a stirred solution of 3.25 g of sodium azide in 12.5 ml of water in an ice-cooled beaker. Gas evolved immediately along with formation of orange oil. After 3–4 minutes, the mixture was diluted with water to 400 ml, then extracted with butyl chloride. The butyl chloride solution was washed with water (3 times) and saturated sodium bicarbonate solution, dried (MgSO$_4$) and evaporated to 13.5 g of oil, 2-(4-azidophenyl)-3-methylbutanoic acid, benzyl ester, which began to solidify. The infrared spectrum of the oil shows absorption peaks at 2130 cm$^{-1}$ (azide) and 1740 cm$^{-1}$ (ester carbonyl). Thin-layer chromatography on silica gel-coated plates in chloroform or butyl chloride showed only one spot.

EXAMPLE 6

2-(4-Azidophenyl)-3-methylbutanoic acid

A mixture of 10 g of 2-(4-azidophenyl)-3-methylbutanoic acid, benzyl ester, 25 ml of dioxane, 10 ml of water and 5.2 g of 50% sodium hydroxide was stirred and boiled under reflux for 30 hours. Most of the dioxane was evaporated in vacuum, and the oily residue diluted with water and butyl chloride, and acidified with 4 N HCl. The butyl chloride solution was washed with water (2 times) and saturated brine, dried (MgSO$_4$), and evaporated to a residual oily solid. Stirring with hexane provided 4.3 g of 2-(4-azidophenyl)-3-methylbutanoic acid as a yellowish solid, m.p. 95°–97°. The infrared spectrum shows absorption peaks at 2120 cm$^{-1}$ (azide) and 1715 cm$^{-1}$ (carboxylic acid carbonyl).

EXAMPLE 7

2-(4-Azidophenyl)-3-methylbutanoyl chloride 2-(4-Azidophenyl)-3-methylbutanoic acid, 3.68 g, was dissolved in 15 ml of thionyl chloride. After 45 minutes the solution was heated to a boil, then evaporated in vacuum to a residual oil. The oil was twice dissolved in diethyl ether and evaporated in vacuum to a residual oil, and further dried under a nitrogen stream. The infrared spectrum of the oil showed absorption peaks at 2120 cm$^{-1}$ (azide) and 1810 cm$^{-1}$ (acid chloride).

EXAMPLE 8

2-(4-Azidophenyl)-3-methylbutanoic acid, α-cyano-3-phenoxybenzyl ester 2-(4-Azidophenyl)-3-methylbutanoyl chloride, prepared in Example 7, was dissolved in 10 ml of methylene chloride. A solution of 3.79 g of m-phenoxybenzaldehyde cyanohydrin in 10 ml of methylene chloride was added, with cooling by an ice bath, followed by 2.4 ml of triethylamine, causing an exothermic reaction and precipitating white solid. After an hour without cooling, the mixture was evaporated to a residue, which was extracted with diethyl ether, the extract filtered, and the filtrate washed with water and saturated sodium bicarbonate solution, dried (MgSO$_4$), and evaporated to 7.4 g of residual oil, 2-(4-azidophenyl)-3-methylbutanoic acid, α-cyano-3-phenoxybenzyl ester. The infrared spectrum shows absorption peaks at 2130 cm$^{-1}$ (azide) and 1760 cm$^{-1}$ (ester carbonyl). Mass spectral analysis showed a molecular ion, m/e 426, corresponding to the product.

Substitution of an equivalent amount of m-phenoxybenzyl alcohol for the m-phenoxybenzaldehyde cyanohydrin in the above reaction provides 2-(4-azidophenyl)-3-methylbutanoic acid, m-phenoxybenzyl ester.

Formulations

Useful formulations of the compounds of Formula I can be prepared in conventional ways. They include dusts, granules, pellets, solutions, emulsions, wet-table powders, emulsifiable concentrates and the like. Many of these may be applied directly. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

|  | Active Ingredient | Weight Percent Diluent(s) | Surfactant(s) |
|---|---|---|---|
| Wettable Powders | 20–60 | 30–79 | 1–10 |
| Emulsions, Solutions (including Emulsifiable Concentrates) | 1–50 | 40–99 | 0–15 |
| Dusts | 1–25 | 70–99 | 0–5 |
| Granules and Pellets | 1–50 | 50–99 | 0–15 |
| High-Strength Compositions | 90–99 | 0–10 | 0–2 |

Lower or higher levels of active ingredient can, of course, be present depending on the intended use and the physical properties of the compound. For example, many of the compounds are oils or relatively low-melting solids. In these cases, the strength of granules must be limited because of physical handling considerations. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey. The more absorptive diluents are preferred for wettable powders and the denser ones for dusts. Typical liquid diluents and solvents are described in Marsden, "Solvents Guide," 2nd Ed., Interscience, New York, 1950. Solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

J. B. Buchanan, U.S. Pat. No. 3,576,834, Apr. 27, 1971, Col. 5, Lines 36 through Col. 7, Line 70 and Examples 1–4, 17, 106, 123–140;

R. R. Shaffer, U.S. Pat. No. 3,560,616, Feb. 2, 1971, Col. 3, Line 48 through Col. 7, Line 26 and Examples 3–9, 11–18;

E. Somers, "Formulation", Chapter 6 in Torgeson, "Fungicides", Vol. I, Academic Press, New York, 1967.

EXAMPLE 9

| Emulsifiable Concentrate | |
|---|---|
| 2-(4-azidophenyl)-3-methylbutanoic acid, α-cyano-3-phenoxybenzyl ester | 30% |
| Blend of oil-soluble sulfonates and polyoxyethylene ethers | 4% |
| Xylene | 66% |

The ingredients are combined and stirred to produce a solution. A fine screen filter is included in packaging line to remove any extraneous undissolved material. The product may be emulsified in water for application.

EXAMPLE 10

| Solution | |
|---|---|
| 2-(4-azidophenyl)-3-methylbutanoic acid, 3-phenoxybenzyl ester | 40% |
| Isophorone | 60% |

The ingredients are combined to produce a solution, which may be applied directly or diluted with aromatic naphtha for spray application.

EXAMPLE 11

| Wettable Powder | |
| --- | --- |
| 2-(4-azidophenyl)-3-methylbutanoic acid, α-cyano-3-phenoxybenzyl ester | 40% |
| Hydrous calcium silicate | 56.5% |
| Sodium lignisulfonate | 3% |
| Sodium dioctylsulfosuccinate | 0.5% |

The active ingredient is warmed so that it may be sprayed on the calcium silicate diluent in a blender. The surfactants are then added and the product passed through a hammer mill to insure uniformity. The product may be dispersed in water for application.

EXAMPLE 12

| Dust Concentrate | |
| --- | --- |
| 2-(4-azidophenyl)-3-methylbutanoic acid, α-cyano-3-phenoxybenzyl ester | 25% |
| Xylene | 1% |
| Diatomite | 29% |
| Kaolinite | 45% |

The active ingredient, diluted with a little xylene, is sprayed upon the diluents in a ribbon blender. The concentrate may be further diluted for field application.

EXAMPLE 13

| Field Strength Dust | |
| --- | --- |
| Dust concentration (Example 12) | 10% |
| Pyrophyllite (powder) | 90% |

The ingredients are blended thoroughly in a ribbon blender to produce a dust containing 2.5% active ingredient.

EXAMPLE 14

| Granule | |
| --- | --- |
| 2-(4-azidophenyl)-3-methylbutanoic acid, 3-phenoxybenzyl ester | 8% |
| Aromatic naphtha | 7.7% |
| Blend of oil-soluble sulfonate and polyoxyethylene ethers | 0.3% |
| Granular diatomite | 84% |

The active ingredient and surfactant are dissolved in the solvent and sprayed upon the granules while blending in a double cone blender. The granules release the active ingredient in the presence of water or soil moisture.

EXAMPLE 15

| Aerosol | |
| --- | --- |
| 2-(4-azidophenyl)-3-methylbutanoic acid, α-cyano-3-phenoxybenzyl ester | 2% |
| Xylene | 2% |
| Dichlorodifluoromethane | 56% |
| Trichlorofluoromethane | 40% |

The xylene solution of active is combined under pressure with the fluorocarbon propellant and packed in aerosol disperser containers.

Use

The compounds of Formula I are useful in control of insects detrimental to agriculture and public health.

The compounds readily control pestiferous insects belonging but not limited to such orders as Lepidoptera, Homoptera, Diptera, Orthoptera and Coleoptera. More specifically, insects controlled by the compounds of this invention include, but are not limited to southern armyworm (*Spodoptera eridania*), bean aphid (*Aphis fabae*), six spotted aster leafhopper (*Macrosteles fascifrons*), housefly (*Musca domestica*), German Cockroach (*Blattella germonica*), black carpet beetle (*Attagenus piceus*), confused flour beetle (*Tribolium confusum*), granary weevil (*Sitophilus granarius*) and boll weevil (*Anthonomus grandis*).

The insects are controlled by applying an insecticidally effective amount of the compound to the locus of infestation, to the area to be protected, or to the pests themselves. For the control of insects in agricultural crops, a compound of Formula I is generally applied to the foliage or other plant parts which are infested or which are to be protected. Insecticidally effective amounts to be applied depend upon the species to be controlled, its life stage, its size and location, the amount of rainfall, the time of year, moisture, temperature, type of application, and other variables. In general, 0.025 to 4 kg/ha may be required for insect control in agriculture with rates of 0.05 to 1 kg/ha usually being sufficient in many situations. In large-scale field operations, rates in the range of 0.05 to 0.5 kg/ha are generally used.

The compounds of this invention will generally be used in formulation with a carrier that commonly will contain oil or water. Applications may be made with concentrated or dilute suspensions of the insecticide in the carrier. Low-volume applications utilizing formulations containing about 20% of the active ingredient may be preferred by some applicators while others may prefer dilute suspensions containing only 5 ppm in high-volume applications.

Conventionally, the compounds will be incorporated into a formulation in a known manner with incorporation of other components such as (a) surfactants, (b) diluents, (c) additives to reduce foam or corrosion, or (d) preservatives to control microbiological growth.

The compound of this invention can be mixed with fungicides, bactericides, acaricides, nematicides, insecticides, or synergists or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides
  methyl 2-benzimidazolecarbamate (carbendazim)
  tetramethylthiuram disulfide (thiuram)
  n-dodecylguanidine monoacetate (dodine)
  manganese ethylenebisdithiocarbamate (maneb)
  1,4-dichloro-2,5-dimethoxybenzene (chloroneb)
  methyl 1-(butylcarbamoyl)-2-benzimidazolecarbamate (benomyl)
  N-trichloromethylthiotetrahydrophthalimide (captan)
  N-(trichloromethylthio)phthalimide (folpet)
Bactericides tribasic copper sulfate
streptomycin sulfate Acaricides
  senecioic acid, ester with 2-sec-butyl-4,6-dinitrophenol (Morocide ®)
  6-methyl-1,3-dithiolo[2,3-β]quinonolin-2-one (Morestan ®)
  ethyl 4,4'-dichlorobenzilate (Chlorobenzilate ®)
  1,1-bis(p-chlorophenyl)-2,2,2-trichloroethanol (Kelthane ®)
  bis(pentachloro-2,4-cyclopentadien-1-yl) (Pentac ®)
  tricyclohexyltin hydroxide (Plictran ®)

Nematicides
  S-methyl 1-(dimethylcarbamoyl)-N-(methylcarbamoyloxy)thioformimidate (Vydate ®)
  S-methyl 1-carbamoyl-N-(methylcarbamoyloxy)thioformimidate
  N-isopropylphosphoramidic acid, O-ethyl-O'-[4-(methylthio)-m-tolyl]diester (Nemacur ®)

Insecticides
  methylcarbamic acid, ester with 2,3-dihydro-2,2-dimethyl-7-benzofuranol (Furadan ®)
  O-[2-chloro-1-(2,4,5-trichlorophenyl)vinyl]phosphoric acid, O',O'-dimethyl ester (Gardona ®)
  2-mercaptosuccinic acid, diethyl ester S-ester with thionophosphoric acid, dimethyl ester (Malathion ®)
  phosphorothioic acid, O,O-dimethyl, O-p-nitrophenyl ester (methyl parathion)
  methylcarbamic acid, ester with α-naphthol (Sevin ®)
  methyl N-[(methylamino)carbonyloxy]ethanimidothioate (methomyl)
  N'-(4-chloro-o-tolyl)-N,N-dimethylformamidine (Galecron ®)
  O,O-diethyl-O-(2-isopropyl-4-methyl-6-pyrimidinyl)phosphorothioate (Diazinon ®)

Synergists
  piperonyl butoxide
  sesamex
  1-methyl-2-(3,4-methylenedioxyphenyl)ethyl octyl sulfoxide
  chlordimeform
  acephate

EXAMPLE 16

Leaves of red kidney bean plants were lightly sprayed with acetone-water dispersions of 2-(4-azidophenyl)-3-methylbutanoic acid, α-cyano-3-phenoxybenzyl ester, at the dilutions indicated. After drying, the leaves were infested with southern armyworm larvae (SAW) 13 mm in length. Insect mortality and percent of the plant consumed was assessed after 72 hours and is recorded below.

| Concentration % Active Ingredient | % Mortality SAW | % Feeding by SAW |
|---|---|---|
| 0.2 | 100 | 2 |
| 0.005 | 90 | 3 |

EXAMPLE 17

Housefly (HF), German Cockroach (GCR), boil weevil (BW), black carpet beetle (BCB), confused flour beetle (CFB) and granary weevil (GW) adults were lightly sprayed with acetone-water dispersions of 2-(4-azidophenyl)-3-methylbutanoic acid, α-cyano-3-phenoxybenzyl ester at the dilutions indicated. Insect mortality was assessed after 24 to 48 hours and is recorded below.

| Concentration % Active Ingredient | % Mortality | | | | | |
|---|---|---|---|---|---|---|
| | HF 24 hrs. | GCR 48 hrs. | BW 48 hrs. | BCB 48 hrs. | CFB 48 hrs. | GW 48 hrs. |
| 0.2 | 100 | — | 100 | — | — | — |
| 0.05 | 100 | 90 | — | 100 | 100 | 85 |
| 0.005 | 100 | 75 | — | 100 | 100 | 80 |

EXAMPLE 18

Leaves of nastercium, pinto beans or young rice plants were lightly sprayed with acetone-water dispersions of 2-(4-azidophenyl)-3-methylbutanoic acid, α-cyano-3-phenoxybenzyl ester at the dilutions indicated. The nastercium and pinto bean leaves were pre-infested with bean aphid (BA) or two spotted mite (TSM), respectively, and the rice plants were infested with six spotted aster leafhopper (SSAL) after the plants had been allowed to dry. Insect mortality was assessed after 48 hours and is recorded below.

| Concentration % Active Ingredient | % Mortality | | |
|---|---|---|---|
| | BA | TSM | SSAL |
| 0.2 | 100 | 100 | 100 |
| 0.0005 | 92 | — | — |

What is claimed is:

1. The compound 2-(4-azidophenyl)-3-methylbutanoic acid, α-cyano-3-phenoxybenzyl ester.

2. The compound 2-(4-azidophenyl)-3-methylbutanoic acid, 3-phenoxybenzyl ester.

3. A composition suitable for control of insects comprising an insecticidally effective amount of the compound of either of claim 1 or 2 and at least one of (a) a diluent and (b) a surfactant.

4. A method for control of insects which comprises applying to a locus of infestation, to the area to be protected or to the pests themselves, an insecticidally effective amount of the compound of either claim 1 or 2.

* * * * *